US00PP21985P2

(12) United States Plant Patent
van Kleinwee

(10) Patent No.: US PP21,985 P2
(45) Date of Patent: Jun. 21, 2011

(54) ***PETUNIA* PLANT NAMED 'PETLILAV'**

(50) Latin Name: *Petunia hybrida*
Varietal Denomination: Petlilav

(75) Inventor: Theodorus Cornelis van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,335

(22) Filed: Jul. 20, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Kent L Bell
(74) *Attorney, Agent, or Firm* — S. Matthew Edwards

(57) ABSTRACT

A new *Petunia* plant named 'Petlilav' particularly distinguished by the medium-sized light purple flowers that have bold red-purple veining and throat color, early flowering and good floriferousness, medium yellow green foliage, excellent branching and an outwardly spreading plant habit with exceptional cold tolerance.

1 Drawing Sheet

Latin name of the genus and species of the plant claimed: *Petunia hybrida.*

Varietal denomination: 'Petlilav'.

BACKGROUND OF THE NEW PLANT

The present invention comprises a new *Petunia*, botanically known as *Petunia hybrida*, and hereinafter referred to by the variety name 'Petlilav'.

'Petlilav' is a product of a planned breeding program. The new cultivar has medium-sized light purple flowers with bold red-purple veining and throat color, early flowering and good floriferousness, medium yellow-green foliage, excellent branching and an outwardly spreading plant habit with exceptional cold tolerance.

'Petlilav' originated from a hybridization made in August 2004 in a controlled breeding environment in Enkhuizen, Netherlands. The female parent was the proprietary, unpatented plant designated 'D1353-1' with lavender colored flowers, more trailing and less vigorous plant habit.

The male parent of 'Petlilav' is the proprietary, unpatented plant designated 'Z2393-1' with pink flower color and less branching plant habit. The resultant seed was sown in February 2005.

'Petlilav' was selected as one flowering plant within the progeny of the stated cross in May 2005 in a controlled environment in Enkhuizen, Netherlands.

The first act of asexual reproduction of 'Petlilav' was accomplished when vegetative cuttings were propagated from the initial selection in May 2005 in a controlled environment in Enkhuizen, Netherlands.

BRIEF SUMMARY OF INVENTION

Horticultural examination of plants grown from cuttings of the plant initiated in May 2005, and continuing thereafter, has demonstrated that the combination of characteristics as herein disclosed for 'Petlilav' are firmly fixed and are retained through successive generations of asexual reproduction.

'Petlilav' has not been observed under all possible environmental conditions. The phenotype may vary significantly with variations in environment such as temperature, light intensity and day length.

A Plant Breeder's Rights for this cultivar was applied for in Canada on Feb. 9, 2010 (#10-6827). 'Petlilav' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Petlilav' with colors being as true as possible with an illustration of this type. The photographic drawing shows a flowering plant growing in a 4 inch pot.

DETAILED BOTANICAL DESCRIPTION

The aforementioned photographs were taken in April 2010 of plants growing in a greenhouse trial in Gilroy, Calif. These plants were approximately 13-14 weeks of age. The plant descriptions and measurements were taken later on those very same plants in mid June 2010 after growing outdoors a few weeks. They were about 17-18 weeks of age.

Color references are made to The Royal Horticultural Society Colour Chart (R.H.S.) 2001.

TABLE 1

DIFFERENCES BETWEEN THE NEW VARIETY 'PETLILAV' AND A SIMILAR VARIETY

| | 'Petlilav' | 'Petlavve' (U.S. Plant Pat. No. 17,291) |
|---|---|---|
| Corolla tube length: | 2.0-2.2 cm | 3.0 cm |
| Anther color: | RHS 85B | RHS 94C |
| Pollen color: | RHS N187C | RHS 94C |

Plant:

*Form, growth and habit.*—Initially semi-mounded to later outwardly spreading, strong vigorous habit, well branched, small foliage, and continuously flowering.

*Plant height.*—10-12 cm.
*Plant height (inflorescence included).*—18-24 cm.
*Plant width.*—38-42 cm.
*Garden performance and tolerance to weather.*—Very good.
*Crop time to flowering.*—About 8-9 weeks.

Roots:
*Number of days to initiate roots and produce a rooted cutting.*—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—Closest to RHS 146A.
*Lower surface.*—Closest to RHS 146B.
*Mature, leaf color, upper surface.*—Closest to RHS 146A.
*Lower surface.*—Closest to RHS 146B.
*Length.*—3-4 cm.
*Width.*—1.7-2.0 cm.
*Shape.*—Ovate.
*Base shape.*—Acuminate.
*Apex shape.*—Acute.
*Margin.*—Entire.
*Texture, upper surface.*—Slightly pubescent; glandular hairs.
*Lower surface.*—Slightly pubescent; glandular hairs.
*Color of veins, upper surface.*—RHS 144A.
*Color of veins, lower surface.*—RHS 144A.
*Petiole color.*—RHS 144A.
*Length.*—0.3-0.5 cm.
*Diameter.*—0.2 cm.
*Texture.*—Slightly pubescent; glandular hairs.

Stem:
*Color of stem.*—RHS 146B.
*Length of stem.*—34-36 cm.
*Diameter.*—0.2-0.3 cm.
*Length of internodes.*—2-5 cm.
*Texture.*—Slightly pubescent; glandular hairs.
*Color of peduncle.*—Between RHS 146C and RHS 146A.
*Length of peduncle.*—1.5-2.5 cm.
*Peduncle diameter.*—0.15 cm.
*Texture.*—Slightly pubescent; glandular hairs.

Inflorescence:
*Type.*—Flowers appear solitary in upper leaf axis.
*Floret type.*—Funnel-shaped; 5 lobed petals; fused at the base; calyx, 5 deeply lobed sepals.
*Blooming habit.*—Continuous throughout the growing season. Good floriferousness.
*Quantity of inflorescences per plant.*—About 100 plus numerous buds.
*Lastingness of individual blooms on the plant.*—5-7 days.
*Fragrance.*—Slightly sweet.

Bud (just when opening/showing color):
*Color.*—RHS 144A to RHS 144B; RHS 155C apex and a hint of RHS N186C basally.
*Length.*—4-4.5 cm.
*Width.*—0.5-0.7 cm.
*Shape.*—Oblong.

Immature inflorescence:
*Diameter.*—4.5-5.0 cm.
*Color, upper surface.*—RHS 75C overlaid with RHS 75B but a hint more of red; sometimes margins of about RHS N74.
*Lower surface.*—Between RHS 75B to RHS 75C.

Mature inflorescence:
*Floret horizontal diameter.*—6.0-6.5 cm.
*Vertical depth.*—About 4.0 cm.
*Petal color, upper surface.*—RHS 75C overlaid with RHS 75B but a hint more of red with sometimes margins of about RHS N74A to RHS N74B with lots of veining closest to RHS N74A but a little more red.
*Lower surface.*—Closest to RHS 75C.
*Petal apex shape.*—Mucronulate.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Papillose.
*Corolla tube color inside.*—RHS 83A to RHS 83B.
*Outside.*—RHS 75D overlaid with a muddy hue of about RHS 77B; and mid-veins of RHS 144B to RHS 144C.
*Corolla tube length.*—2.0-2.2 cm.
*Corolla texture, inside.*—Papillose.
*Outside.*—Glandular hairs; pilose.

Calyx:
*Color, upper surface.*—RHS 146B.
*Lower surface.*—RHS 146B.
*Length.*—1.0-1.2 cm.
*Width.*—0.25 cm.
*Shape.*—Ligulate.
*Apex shape.*—Obtuse.
*Based.*—Fused.
*Margins.*—Entire.
*Texture, upper surface.*—Glandular hairs.
*Lower surface.*—Glandular hairs.

Reproductive organs:
*Pistil.*—1.
*Length.*—2.0-2.1 cm.
*Style color.*—RHS 1N55B but more grey and a hint of RHS 71B at the stigma.
*Style length.*—1.9-2.1 cm.
*Stigma color.*—RHS N81A with RHS 83A on the top.
*Ovary color.*—RHS 144B with RHS 144A at the upper portion.
*Stamens.*—5.
*Color of filaments.*—RHS N155B.
*Length filaments.*—2.0-2.3 cm.
*Anther color.*—RHS 85B but slightly more grey.
*Anther length.*—0.2 cm.
*Anther shape.*—Oval.
*Color of pollen.*—RHS N187C.
*Pollen amount.*—Moderate.
*Fertility/seed set.*—Has not been observed on this hybrid.

Disease/pest resistance: Disease/pest resistance has not been observed on this hybrid.

What is claimed:

1. A new and distinct variety of *Petunia* plant named 'Petlilav' substantially as illustrated and described herein.

* * * * *

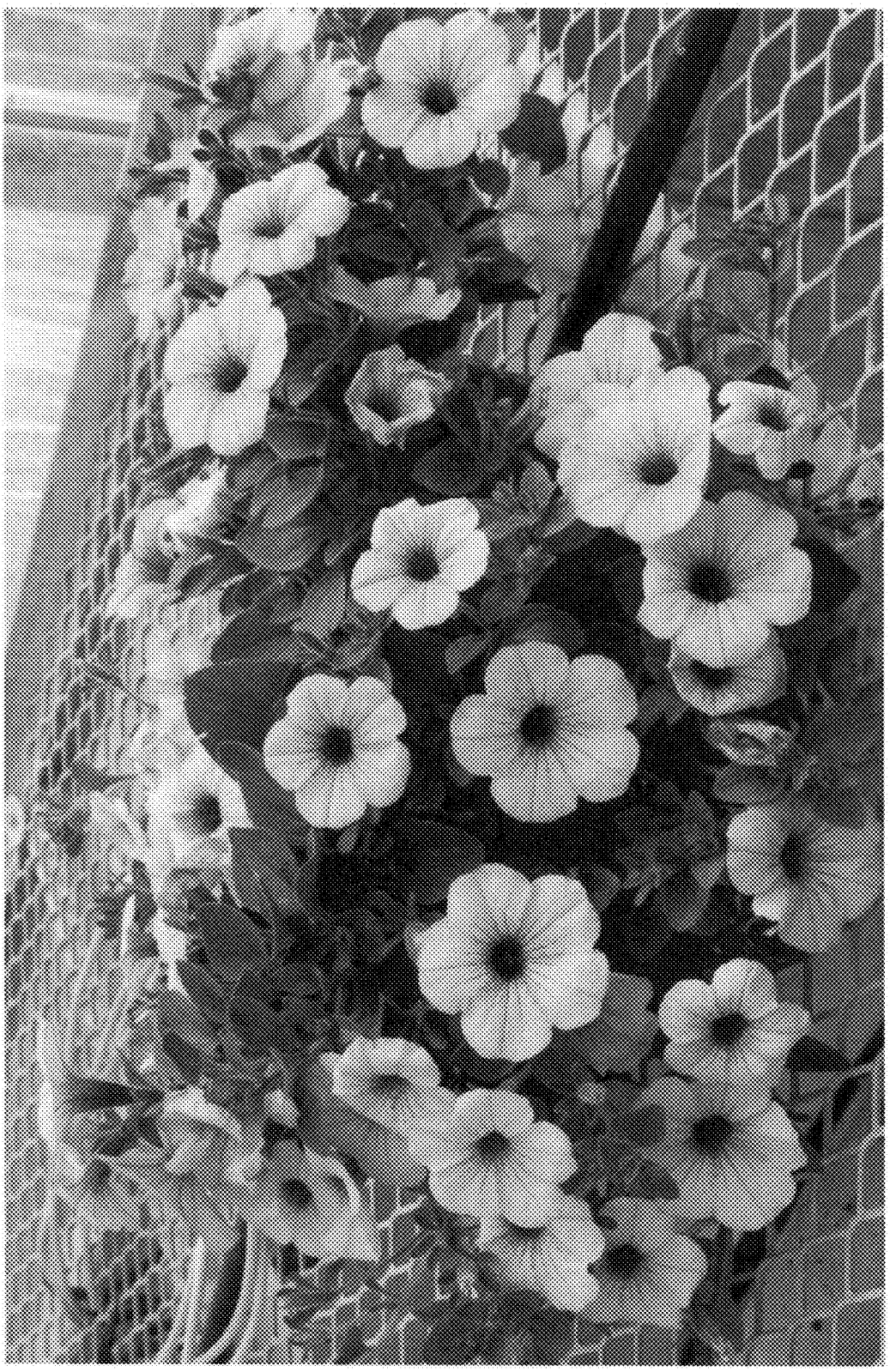

UNITED STATES PATENT AND TRADEMARK OFFICE

CERTIFICATE OF CORRECTION

PATENT NO. : PP21,985 P2
APPLICATION NO. : 12/804335
DATED : June 21, 2011
INVENTOR(S) : van Kleinwee It is certified that error appears in the above-identified patent and that said Letters Patent is hereby corrected as shown below:

IN THE SPECIFICATIONS:

At column 4, line 42, please delete "RHS 1N55B" and insert therefor --RHS N155B--

Signed and Sealed this
Second Day of August, 2011

David J. Kappos

David J. Kappos
*Director of the United States Patent and Trademark Office*